United States Patent
Nelson et al.

(10) Patent No.: US 7,153,493 B2
(45) Date of Patent: Dec. 26, 2006

(54) CLEAR ORAL COMPOSITIONS CONTAINING POTASSIUM SALT

(75) Inventors: Dennis G.A. Nelson, Mountain Lakes, NJ (US); Andrew R Gallopo, Morris Plains, NJ (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 349 days.

(21) Appl. No.: 10/630,526

(22) Filed: Jul. 30, 2003
(Under 37 CFR 1.47)

(65) Prior Publication Data
US 2004/0022745 A1    Feb. 5, 2004

Related U.S. Application Data

(63) Continuation of application No. 10/042,712, filed on Mar. 21, 2002, now abandoned, which is a continuation of application No. 09/503,431, filed on Feb. 14, 2000, now abandoned.

(60) Provisional application No. 60/124,258, filed on Mar. 12, 1999.

(51) Int. Cl.
*A61K 7/16* (2006.01)
(52) U.S. Cl. ..................................... 424/49
(58) Field of Classification Search .................. 424/49
See application file for complete search history.

(56) References Cited

U.S. PATENT DOCUMENTS

| | | |
|---|---|---|
| 3,627,822 A | 12/1971 | Sundby |
| 3,863,006 A | 1/1975 | Hodosh |
| 3,929,579 A | 12/1975 | Yoshimura et al. |
| 3,985,869 A | 10/1976 | Yoshimura et al. |
| 4,057,621 A | 11/1977 | Pashley et al. |
| 4,283,385 A | 8/1981 | Dhabhar et al. |
| 4,346,493 A | 8/1982 | Goudsmit |
| 4,357,318 A | 11/1982 | Shah et al. |
| 4,400,373 A | 8/1983 | Hodosh |
| 4,432,114 A | 2/1984 | Goudsmit |
| 4,581,292 A | 4/1986 | Shinpo et al. |
| 4,618,488 A | 10/1986 | Maeyama et al. |
| 4,631,185 A | 12/1986 | Kim |
| 4,645,662 A | 2/1987 | Nakashima et al. |
| 4,657,758 A * | 4/1987 | Goldemberg et al. ......... 424/49 |
| 4,751,072 A | 6/1988 | Kim |
| 4,756,903 A | 7/1988 | Shozo et al. |
| 4,933,171 A | 6/1990 | Bristow et al. |
| 4,992,258 A | 2/1991 | Mason |
| 5,015,466 A | 5/1991 | Parran, Jr. et al. |
| 5,015,467 A | 5/1991 | Smitherman |
| 5,043,183 A * | 8/1991 | Gershon et al. .............. 424/52 |
| 5,087,444 A | 2/1992 | Jackson et al. |
| 5,098,711 A | 3/1992 | Hill et al. |
| 5,153,006 A | 10/1992 | Hodosh |
| 5,160,737 A | 11/1992 | Friedman et al. |
| 5,165,913 A | 11/1992 | Hill et al. |
| 5,178,870 A | 1/1993 | Schaeken et al. |
| 5,182,099 A | 1/1993 | Jonsson et al. |
| 5,188,820 A | 2/1993 | Cummins et al. |
| 5,188,822 A * | 2/1993 | Viccaro et al. ............... 424/52 |
| 5,227,154 A | 7/1993 | Reynolds |
| 5,229,103 A * | 7/1993 | Eagle et al. ................... 424/49 |
| 5,240,696 A | 8/1993 | Van Der Ouderaa et al. |
| 5,240,697 A | 8/1993 | Norfleet et al. |
| 5,242,693 A | 9/1993 | Kurihara et al. |
| 5,252,577 A | 10/1993 | Breuer et al. |
| 5,256,402 A | 10/1993 | Prencipe et al. |
| 5,258,173 A | 11/1993 | Waterfield |
| 5,270,031 A | 12/1993 | Lim et al. |
| 5,275,805 A | 1/1994 | Nabi et al. |
| 5,284,648 A | 2/1994 | White et al. |
| 5,296,215 A | 3/1994 | Burke et al. |
| 5,310,542 A | 5/1994 | Au et al. |
| 5,328,682 A | 7/1994 | Pullen et al. |
| 5,338,538 A * | 8/1994 | Tricca et al. ................... 424/57 |
| 5,352,439 A | 10/1994 | Norfleet et al. |
| 5,362,480 A | 11/1994 | Au et al. |
| 5,374,417 A | 12/1994 | Norfleet et al. |
| 5,403,577 A | 4/1995 | Friedman |
| 5,409,902 A | 4/1995 | Carson et al. |
| 5,416,075 A | 5/1995 | Carson et al. |
| 5,437,858 A | 8/1995 | Hungerbach et al. |
| 5,438,076 A | 8/1995 | Friedman et al. |
| 5,449,509 A | 9/1995 | Jackson et al. |
| 5,451,401 A | 9/1995 | Zerby et al. |
| 5,486,350 A | 1/1996 | Norfleet et al. |
| 5,487,906 A | 1/1996 | Dixit et al. |
| 5,490,978 A | 2/1996 | Spaltro et al. |
| 5,500,448 A | 3/1996 | Cummins et al. |
| 5,503,823 A | 4/1996 | Norfleet et al. |

(Continued)

FOREIGN PATENT DOCUMENTS

EP    1040819 A2 *  10/2000

(Continued)

*Primary Examiner*—Ralph Gitomer
(74) *Attorney, Agent, or Firm*—Evan J. Federman; Darryl C. Little

(57) ABSTRACT

The subject invention provides compositions useful in oral cavity, comprising an effective amount of a soluble potassium salt, a sodium ($C_2$–$C_{24}$) alkylsulfate in an amount effective to remove or loosen debris and/or stains from a surface, and a polar surfactant, said surfactant comprising a hydrophobic portion selected from a ($C_6$–$C_{30}$) alkyl group and a polymeric silicone group, wherein the molar ratio of the surfactant to the sodium ($C_8$–$C_{24}$) alkylsulfate is greater than or equal to about 1:1. The subject invention also provides a mint flavoring that does not comprise a substantial amount of menthol, said mint flavoring being either a dementholated natural mint extract or a synthetic blend.

9 Claims, No Drawings

U.S. PATENT DOCUMENTS

| | | |
|---|---|---|
| 5,505,933 A | 4/1996 | Norfleet et al. |
| 5,522,726 A | 6/1996 | Hodosh |
| 5,534,243 A | 7/1996 | Dixon, Jr. et al. |
| 5,534,244 A | 7/1996 | Tung |
| 5,560,905 A | 10/1996 | Lukacovic |
| 5,565,190 A | 10/1996 | Santalucia et al. |
| 5,571,501 A | 11/1996 | Toy |
| 5,578,293 A | 11/1996 | Prencipe et al. |
| 5,578,294 A | 11/1996 | Lukacovic |
| 5,589,159 A | 12/1996 | Markowitz et al. |
| 5,589,160 A | 12/1996 | Rice |
| 5,597,552 A | 1/1997 | Herms et al. |
| 5,599,525 A | 2/1997 | Hsu et al. |
| 5,599,527 A | 2/1997 | Hsu et al. |
| 5,603,920 A | 2/1997 | Rice |
| 5,681,549 A * | 10/1997 | McLaughlin et al. ......... 424/54 |
| 5,686,063 A * | 11/1997 | McLaughlin et al. ......... 424/54 |
| 5,695,745 A * | 12/1997 | Barton et al. ................. 424/49 |
| 5,756,074 A | 5/1998 | Ascione et al. |
| 5,827,505 A * | 10/1998 | Hughes et al. ................ 424/49 |
| 5,833,956 A * | 11/1998 | Gorlin et al. ................. 424/49 |
| 6,004,538 A * | 12/1999 | Hughes et al. ................ 424/49 |
| 6,193,958 B1 * | 2/2001 | Edwards et al. .............. 424/49 |
| 6,432,388 B1 * | 8/2002 | Alvarez Hernandez ...... 424/50 |

FOREIGN PATENT DOCUMENTS

| | | |
|---|---|---|
| JP | 8551380 | 6/1980 |
| JP | 11191187 | 5/1987 |
| JP | 2221690 | 1/1990 |
| JP | 9286094 | 4/1994 |
| JP | 1243897 | 1/1997 |
| JP | 17596697 | 7/1997 |
| WO | WO 9304663 | 3/1993 |
| WO | 94 08559 A1 * | 4/1994 |
| WO | WO 9412599 | 6/1994 |
| WO | WO 9421767 | 12/1994 |
| WO | WO 9421768 | 12/1994 |
| WO | WO 9421770 | 12/1994 |

* cited by examiner

US 7,153,493 B2

CLEAR ORAL COMPOSITIONS CONTAINING POTASSIUM SALT

This application is a continuation U.S. patent application Ser. No. 10/042,712, filed on Mar. 21, 2002, now abandoned which is a continuation of U.S. patent application Ser. No. 09/503,431, filed on Feb. 14, 2000, now abandoned which claims the benefit of U.S. Provisional Patent Application No. 60/124,258, filed on Mar. 12, 1999, the entirety of which is hereby incorporated by reference as if fully set forth herein.

FIELD OF THE INVENTION

The present invention relates to detergent compositions useful in the healthcare and hard surface and fabric cleaning fields.

BACKGROUND OF THE INVENTION

Sodium alkylsulfate surfactants, e.g., sodium lauryl sulfate (SLS), are generally not substantially compatible with compounds that contain potassium because an insoluble potassium alkyl sulfate precipitate forms when the sodium alkylsulfate is combined with a potassium salt. While the solubility of SLS in water is about 10% on a gram per gram basis, experiments indicate that the solubility of potassium lauryl sulfate is less than approximately 0.02%.

Thus, many aqueous compositions which contain SLS cannot contain a potassium salt which might otherwise be useful as an active ingredient. If the potassium salt and SLS do coexist in a composition, the usefulness of that potassium salt is not being optimized since a portion of the potassium ion of the salt is being occupied in the insoluble potassium lauryl sulfate precipitate. Alternatively, if a potassium salt is a required ingredient in a composition, nonionic surfactants can be used instead of SLS to avoid a potassium lauryl sulfate precipitation. However, such nonionic surfactants are in many instances not as effective as SLS as wetting or cleaning agents. For example, oral care compositions which contain nonionic surfactants instead of SLS are not as effective in removing dental plaque. It would thus be beneficial in the healthcare and surface and fabric cleaning fields if SLS could be combined with a potassium salt without forming an insoluble potassium lauryl sulfate precipitate.

Numerous potassium salts are useful in detergent compositions. Potassium pyrophosphate salts, for example, can have detergent building activity in detergent compositions that comprise a wetting agent such as SLS. However, the detergent building activity of the potassium pyrophosphate salt in such compositions may not be optimal due to the formation of the potassium lauryl sulfate precipitate described above. For example, U.S. Pat. No. 5,338,538 to Tricca et al. relates to liquid compositions for loosening and removing plaque that comprise SLS and a detergent builder selected from dialkali metal pyrophosphate salts, tetraalkali metal pyrophosphate salts, and mixtures thereof. The preferred pyrophosphate salts are disodium pyrophosphate and tetrasodium pyrophosphate. It may be useful to be able to add potassium pyrophosphate salts to compositions such as those referred to in U.S. Pat. No. 5,338,538. This is because potassium pyrophosphate salts can be more soluble than sodium pyrophosphate salts and a higher concentration of pyrophosphate in solution could, thus, be achieved. Also, replacing all or some sodium pyrophosphate salt with potassium pyrophosphate would reduce the sodium content of the oral composition, which some consumers may find preferable.

Furthermore, many potassium salts possess therapeutic activities which are useful in healthcare compositions. For example, several potassium salts are believed to possess activity in reducing dental nerve and/or dentin sensitivity. Such potassium salts could therefore be included in oral compositions designed for the treatment of sensitive teeth and gums. U.S. Pat. No. 4,751,072 to Kim, for example, relates to a method for reducing sensory nerve activity in hypersensitive teeth and for desensitizing hypersensitive dentin that involves applying a potassium salt selected from potassium bicarbonate and potassium chloride. Also, U.S. Pat. No. 5,403,577 to Friedman refers to a sustained-release oral composition for treating and preventing dental hypersensitivity comprising an anti-hypersensitivity agent selected from a group of active ingredients including potassium nitrate, potassium bicarbonate, and potassium chloride. Moreover, potassium ions are believed to block nerve conduction in vitro (Peackock, J., and Orchardson, R., 1995, J. Dent. Res. 74(2):634–641). However, any SLS present in such a sensitivity composition comprising a potassium salt may result in the formation of the aforementioned insoluble potassium lauryl sulfate precipitate.

SUMMARY OF THE INVENTION

The subject invention provides an oral composition comprising:
 a) from about 0.01% by weight to about 20% by weight of an active ingredient which is an orally-acceptable, soluble potassium salt;
 b) from about 0.01% by weight to about 10% by weight of a sodium ($C_8$–$C_{24}$) alkylsulfate;
 c) from about 0.01% by weight to about 20% by weight of an orally-acceptable polar surfactant, said surfactant comprising a hydrophobic portion selected from a ($C_6$–$C_{30}$) alkyl group and a polymeric silicone group; and
 d) an orally-acceptable aqueous vehicle;
 wherein the molar ratio of the surfactant of (c) to the sodium ($C_8$–$C_{24}$) alkylsulfate of (b) is greater than or equal to about 1:1.

The subject invention further provides an oral composition as recited above, suitable for loosening or removing plaque and/or stains present on dental surfaces, wherein the soluble potassium salt of the composition comprises a potassium pyrophosphate salt in an amount effective, optionally in combination with other pyrophosphate salts, to remove or loosen plaque and/or stains when the composition is orally applied to a dental surface.

The subject invention further provides an oral composition as recited above, suitable for reducing dental nerve and/or dentin sensitivity, wherein the soluble potassium salt of the composition comprises a potassium salt capable of reducing dental nerve and/or dentin sensitivity in an amount effective to reduce dental nerve and/or dentin sensitivity when the composition is orally applied to a dental surface.

The subject invention further provides an oral composition for reducing dental nerve and/or dentin sensitivity comprising an effective amount of an ingredient that possesses activity in reducing dental nerve and/or dentin sensitivity, an orally-acceptable vehicle, and a flavoring that does not contain a substantial amount of menthol, said flavoring in an amount effective to provide flavor to said composition.

The subject invention further provides a mint flavoring that does not comprise a substantial amount of menthol, said mint flavoring being either a dementholated natural mint extract or a synthetic blend.

The subject invention further provides an aqueous detergent composition comprising an effective amount of an active ingredient that is a soluble potassium salt, a sodium ($C_8$–$C_{24}$) alkylsulfate in an amount effective to remove or loosen debris and/or stains from a surface, and a polar surfactant, said surfactant comprising a hydrophobic portion selected from a ($C_6$–$C_{30}$) alkyl group and a polymeric silicone group, wherein the molar ratio of the surfactant to the sodium ($C_8$–$C_{24}$) alkylsulfate is greater than or equal to about 1:1.

The subject invention further provides a method for inhibiting the formation of a potassium alkylsulfate precipitate in an aqueous composition comprising a soluble potassium salt and a sodium ($C_8C_{24}$) alkylsulfate, which method comprises including a polar surfactant in said composition in an amount of about equal to or greater than the amount of sodium ($C_8$–$C_{24}$) alkylsulfate in the composition, which polar surfactant comprises a hydrophobic portion selected from the group consisting of a ($C_6$–$C_{30}$) alkyl group and a polymeric silicone group.

The subject invention further provides a method of loosening and/or removing dental plaque and/or stains while simultaneously reducing dental nerve and/or dentin sensitivity in an oral cavity of a mammal, comprising administering to the oral cavity of said mammal an effective amount of an oral composition as described herein.

The subject invention further provides a method of loosening and/or removing dental plaque and/or stains in an oral cavity of a mammal, comprising administering to the oral cavity of said mammal an effective amount of an oral composition as described herein.

The subject invention further provides a detergent composition as described herein, suitable for loosening and/or removing dirt, debris, and/or stains from skin and/or hair.

The subject invention further provides a method of loosening and/or removing dirt, debris, and/or stains from skin or hair, comprising administering to said skin or hair an amount of a composition as described herein effective in removing or loosening dirt, debris, or stains.

The subject invention further provides a detergent composition as described herein, suitable for loosening and/or removing dirt, debris, and/or stains from a hard surface and/or a fabric.

The subject invention further provides a method of loosening or removing dirt, debris, and/or stains from a hard surface or a fabric, comprising administering to said hard surface or fabric an amount of a composition as described herein effective in removing or loosening dirt, debris, or stains.

DETAILED DESCRIPTION OF THE INVENTION

The subject invention provides an oral composition which comprises a sodium alkylsulfate and a potassium salt, said compositions further comprising a surfactant in order to inhibit the formation of a potassium lauryl sulfate precipitate.

The subject invention can, however, be applied to any composition, not just oral compositions, that contains both a sodium ($C_8$–$C_{24}$) alkylsulfate and a potassium salt. For example, the subject invention can also have applications in hair and/or body shampoos, bubble baths, shaving creams, dishwashing detergents, upholstery cleaners (such as, fabric, vinyl, and leather cleaners), carpet detergents, laundry detergents, and hard surface cleaners. All of the aforementioned compositions possess detergent properties, either as a primary function (as in the case of, for example, a shampoo) or a secondary function (as in the case of, for example, a shaving cream), and all can use a sodium alkylsulfate, such as SLS, as a wetting agent. Therefore, any such composition could benefit from the present invention, which permits the inclusion of a soluble potassium salt, e.g. a potassium pyrophosphate salt, that can impart desirable characteristics to said composition, for example enhanced detergent capability.

Accordingly, the subject invention also provides a detergent composition comprising an effective amount of a soluble potassium salt, a sodium ($C_8$–$C_{24}$) alkylsulfate, and a polar surfactant, said surfactant comprising a hydrophobic portion selected from the group consisting of a ($C_6$–$C_{30}$) alkyl group and a polymeric silicone group, wherein the molar ratio of the surfactant to the sodium ($C_8$–$C_{24}$) alkylsulfate is greater than or equal to about 1:1. The subject invention further provides a method for inhibiting the formation of a potassium alkylsulfate precipitate from forming in a composition comprising a soluble potassium salt and a sodium ($C_8$–$C_{24}$) alkylsulfate, which method comprises including a polar surfactant in said composition in an amount of about equal to or greater than the amount of sodium ($C_8$–$C_{24}$) alkylsulfate in the composition, which polar surfactant comprises a hydrophobic portion selected from a ($C_6$–$C_{30}$) alkyl group and a polymeric silicone group.

As used herein, the term "detergent composition" refers to a composition which has as either a primary or a secondary function the ability to loosen or remove debris and/or stains from a surface. In one embodiment, a detergent composition of the present invention is an oral composition.

As used herein, unless otherwise indicated, the term "oral composition" refers to a detergent composition, as defined above (having a detergent property as either a primary or secondary function), useful for oral care, including compositions for the care of teeth and/or gums. Examples of forms the detergent compositions of the present invention can have include gels, pastes, and liquids (oral rinses). The term "gel" refers to a visually-clear semisolid composition. Gels according to this invention can have various viscosities. One of ordinary skill can also formulate the compositions of the present invention into other forms that are known in the art. Examples of other forms include, but are not limited to, creams, tablets, and granulations.

Oral compositions of the present invention include, for example, dentifrices. A dentifrice is a composition, in a form such as a paste or gel, which composition comprises an abrasive, and which composition is useful for removing and/or loosening plaque, debris and/or stains from teeth and gums. Other oral compositions of the invention include oral rinses, for example mouthwashes for treating oral malodor and rinses that have as their primary function detergent properties for removal and/or loosening of plaque. "Oral rinses" are to be distinguished from dentifrices in that oral rinses do not include an abrasive.

The amounts of ingredients and the solubilities recited as percentages throughout this application, unless otherwise indicated, refer to the amount by weight of such ingredient or solute compared to the total weight of the composition containing the ingredient or solute. For example, a composition comprising from about 0.01% by weight to about 20% by weight of an orally-acceptable polar surfactant comprises from about one ten-thousandth to about two tenths of a gram of the polar surfactant per gram of the total composition (i.e., from about one one-hundredth to about 20 grams of the polar surfactant per 100 grams of total composition).

A composition of the present invention comprises a soluble potassium salt as an active ingredient. The term "active ingredient" refers to, unless otherwise indicated, any substance that possesses a therapeutic, hygienic or cosmetic activity in a detergent composition (for example an oral composition), or possesses an activity that enhances the aesthetic or sensory properties of the detergent composition, or possesses activity that enhances the detergent properties of the detergent composition. For example, certain potassium salts, such as potassium sorbate, possess bacteriostatic activity and can therefore be an active ingredient because they are useful in a detergent composition as a preservative. As another example, certain potassium salts, such as potassium pyrophosphate salts, have mineral-chelating activity in water and can serve as an active ingredients because they behave as detergent builders, enhancing the ability of the sodium alkylsulfate in the detergent composition to remove and loosen debris, such as plaque, and/or stains. Other potassium salts, such as potassium nitrate and potassium chloride, can be an active ingredient because they can reduce dental nerve and/or dentin sensation. Still other potassium salts, for example potassium phosphate, can be an active ingredient because they can buffer a detergent composition to a selected pH, for example a pH of about 7. Other potassium salts having particular properties known in the art can be selected as an active ingredient, and compositions comprising such potassium salts are part of the subject invention.

If a composition of the present invention is to be applied to the skin and/or hair of a living animal, including a human, then the potassium salt therein must be acceptable for application without harmful side effects when used as intended. Likewise, if the composition is for oral use, then the potassium salt therein must be orally-acceptable, i.e. acceptable for use by humans or other animals in the oral cavity without harmful side effects. Orally-acceptable potassium salts and potassium salts that are acceptable for application to skin and/or hair of living animals can be determined by those of ordinary skill in the art.

The term "orally applied" as used herein, unless otherwise indicated, means application to the oral cavity of a living animal. "Oral application" includes, but is not limited to, brushing the oral cavity and/or teeth in the oral cavity, rinsing the oral cavity and gargling, and spraying into the oral cavity.

A "soluble potassium salt", for purposes of this application and unless otherwise indicated, is any organic or inorganic potassium salt that is soluble in an aqueous solution. Preferably, the soluble potassium salt is any potassium salt that has a solubility of greater than or equal to about 5% in water, meaning that an aqueous composition of the potassium salt (consisting solely of water and the potassium salt) can contain at least about .05 grams of the potassium salt, if not more, in solution. Thus, one hundred grams of an aqueous solution consisting of a potassium salt that is at least about 5% soluble in water contains at least about 5 grams of the potassium salt and at most about 95 grams of water.

The active ingredient is present in the compositions of the present invention in an "effective amount", which means that the ingredient, i.e., the soluble potassium salt, is present in the composition in an amount that is at least sufficient to provide the activity for which the potassium salt has been selected. An effective amount can be determined by one of ordinary skill in the art, for example by preparing a series of pre-formulations, each comprising a different amount of the potassium salt, testing each pre-formulation for the activity of the potassium salt, and determining the minimum amount of the potassium salt required to provide the desired activity. Generally, the amount of soluble potassium salt effective for a hard surface or fabric cleaner is from about 0.1% to about 50%, and for a healthcare composition is from about 0.1% to about 20%.

Some specific examples of orally-acceptable, soluble potassium salts that can be used as an active ingredient in an oral composition of the present invention include potassium pyrophosphate salts, such as dipotassium pyrophosphate, tetrapotassium pyrophosphate, tripotassium pyrophosphate, and monopotassium pyrophosphate. Pyrophosphate salts have activity as detergent builders and thus are useful in loosening and removing plaque and/or stains present on dental surfaces. A composition of the present invention can comprise a combination of pyrophosphate salts, for example a combination of potassium pyrophosphate salts, each of which has activity as a detergent builder. Oral compositions of the present invention can furthermore optionally comprise potassium pyrophosphate salts in combination with other pyrophosphate salts, such as, for example, disodium pyrophosphate or tetrasodium pyrophosphate, to remove or loosen plaque and/or stains when the composition is orally applied to a dental surface.

Other specific examples of potassium salts that can be used in an oral composition of the present invention are potassium salts that are active in reducing dental nerve and/or dentin sensitivity. Potassium salts that possess activity in reducing dental nerve and/or dentin sensitivity are known in the art, and any such potassium salt is useful in the present invention. Examples of potassium salts that are active in reducing dental nerve and/or dentin sensitivity include, but are not limited to, potassium nitrate, potassium citrate, potassium chloride, potassium oxalate, potassium bicarbonate, potassium phosphate, monobasic potassium phosphate, dibasic potassium phosphate, tribasic potassium phosphate, and potassium pyrophosphate salts. Mixtures of such salts can be used in the present invention. In a preferred embodiment, the potassium salt capable of reducing dental nerve and/or dentin sensitivity is potassium nitrate.

A composition of the present invention can comprise a mixture of soluble potassium salts. Each potassium salt in the mixture can have the same or similar activity (for example, they each can have activity as a detergent builder, enhancing removal or loosening of debris and/or stains) or potassium salts in the mixture can have different activities (for example, one salt can have activity as a detergent builder and another salt in the mixture can have activity in reducing dental nerve sensation).

The amount of the soluble potassium salt ranges preferably from about 0.01% by weight to about 20% by weight of a healthcare composition of the present invention, preferably from about 0.1% by weight to about 50% by weight of a hard surface cleaner of the present invention, and preferably from about 0.1% by weight to about 50% by weight of a fabric cleaner composition of the present invention. If the composition is a dentifrice, a preferred amount of potassium salt in such dentifrice is from about 1% to about 10%. If the composition is an oral rinse, a preferred amount of potassium salt in such an oral rinse is from about 0.1% to about 5%.

In specific oral compositions of the present invention for removing and loosening plaque and stains, a potassium pyrophosphate salt is present in the composition in an amount effective, optionally in combination with other pyrophosphate salts as described above, to provide at least about 0.3%, more particularly from about 0.3% to about 5%, by weight $P_2O_7^{-4}$ based on the weight of the total composition. In order to provide this amount of $P_2O_7^{-4}$, compositions of this invention for loosening or removing plaque and/or stains from dental surfaces preferably contain from about 0.02% by weight to about 1% by weight potassium pyrophosphate salt based on the weight of the total composition.

Regarding the sodium alkylsulfate ingredient of the compositions of the present invention, the term "sodium ($C_8$–$C_{24}$) alkylsulfate" refers to any sodium ($C_8$–$C_{24}$) alkylsulfate or mixture of sodium ($C_8$–$C_{24}$) alkylsulfates. The term "alkyl", as used herein, refers to any hydrocarbon, either saturated or unsaturated, and either straight, branched, or cyclic. Reference to a specific sodium ($C_8$–$C_{24}$) alkylsulfate, such as SLS, includes both the pure sodium ($C_8$–$C_{24}$) alkylsulfate as well as various grades of the sodium ($C_8$–$C_{24}$) alkylsulfate which contain relatively small amounts of different sodium ($C_8$–$C_{24}$) alkylsulfates. For example, the term "SLS" includes both compositions of pure SLS as well as various grades of SLS which can contain other sodium alkylsulfates that can have generally from 10 to 14 carbons their alkyl portion and that can further have one or more unsaturated bonds in their alkyl portions. Sodium ($C_8$–$C_{24}$) alkylsulfates, such as SLS, are useful as wetting agents, loosening or removing debris and/or stains, in detergent compositions. When the sodium ($C_8$–$C_{24}$) alkylsulfate is free from interaction with a potassium salt ingredient, as is provided by the present invention, a greater amount of debris and stain removal can be obtained. Examples of sodium ($C_8$–$C_{24}$) alkylsulfates which are useful in the present invention include, but are not limited to, SLS, sodium myristyl sulfate, sodium palmityl sulfate, sodium stearyl sulfate, sodium palmitoleyl sulfate, sodium oleyl sulfate, sodium capryl sulfate, and sodium caprylyl sulfate. The aforementioned sodium ($C_8$–$C_{24}$) alkylsulfates comprise 12, 14, 16, 18, 16 (with one unsaturated carbon-carbon bond), 18 (with one unsaturated carbon-carbon bond), 10, and 8 carbons, respectively. An example of a sodium alkylsulfate having 24 carbons which can be used in the subject invention is sodium nervonyl acid; Preferably, the compositions of the subject invention comprise SLS.

Preferably, the amount of sodium ($C_8$–$C_{24}$) alkylsulfate in a composition of the present invention is from about 0.01% to about 10% by weight of the composition for a healthcare composition, from about 0.1% to about 50% by weight for a hard surface cleaner, and from about 0.1 to about 50% for a fabric cleaner composition. The amount of sodium ($C_8$–$C_{24}$) alkylsulfate of a dentifrice of the subject invention is preferably from about 0.1% to about 5% by weight of the composition. For an oral rinse, the amount of the sodium ($C_8$–$C_{24}$) alkylsulfate ingredient is preferably from about 0.02% by weight to about 2% by weight of the composition. More preferably for a hard surface cleaner, the amount is from about 1% to about 50%, and more preferably for a fabric cleaner from about 1% to about 50%.

The polar surfactant used in the compositions of the present invention can be any polar surfactant that comprises a hydrophobic portion selected from the group consisting of a ($C_6$–$C_{30}$) alkyl group, wherein "alkyl" is as defined above, and a polymeric silicone group. If the composition is for oral use or for application to skin and/or hair of a living animal, then the surfactant must not cause harmful side effects to the animal when used as intended. Determination of surfactants acceptable for such uses is known in the art. A "polar" surfactant for purposes of this invention is a surfactant that comprises a hydrophilic group and a hydrophobic group. Polar surfactants can be anionic, cationic, nonionic or amphoteric. One of ordinary skill in the art can determine whether a surfactant is polar.

A "polymeric silicone group" is any group that comprises repeating units which comprise a silicone atom. In a preferred embodiment, a polymeric silicone group comprises repeating —Si($R^1$)($R^2$)O— units, wherein $R^1$ and $R^2$ of each unit is independently the same or different, and wherein each —Si($R^1$)($R^2$)O— unit in the polymeric silicone group can have the same or different $R^1$ and/or $R^2$ groups, $R^1$ and $R^2$ each being a ($C_1$–$C_6$) alkyl. Preferably each $R^1$ and $R^2$ in a polymeric silicone group is methyl or ethyl. More preferably, each $R^1$ and $R^2$ is a methyl.

Polar surfactants which comprise a hydrophobic portion which is a polymeric silicone group can include, but are not limited to, dimethicone copolyols (i.e., ethoxylated and/or propoxylated polydimethylsiloxane polymers) and derivatives thereof wherein the ethoxylated/propoxylated portion of the compounds is derivatized such as polydimethylsiloxane phosphate esters, polydimethylsiloxane phosphobetaines, polydimethylsiloxane taurates, acetylated polydimethylsiloxane copolyols, and polydimethylsiloxane quaternium compounds. Surfactants comprising a polymeric silicone group are also described, among other places, in Imperante, J. et al., 1994, Cosmetics & Toiletries Vol. 108, No. 4, p. 79, and Imperante, J. et al., 1994, Cosmetics & Toiletries Vol. 109, No. 3, p. 81, which are hereby incorporated by reference in their entireties.

Some specific examples of derivatized polydimethylsiloxane copolyols are sodium dimethicone copolyol acetyl methyltaurate, e.g. PECOSIL™ DCT (Phoenix Chemical, Inc., Somerville, N.J.); dimethicone copolyol myristyl ammonium chloride, e.g. PECOSIL™ SM-40 (Phoenix Chemical, Inc.); and dimethicone copolyol phosphate, e.g. PECOSIL™ PS-100, PECOSIL™ PS-150, and PECOSIL™ PS-200, from Phoenix Chemical, Inc., and SILPHOS™ A100 (Siltech, Norcross, Ga.). As discussed above, other polydimethylsiloxane copolyols are known in the art and can be used in the present invention.

In another embodiment, the polar surfactant comprises a hydrophobic portion comprising a ($C_6$–$C_{30}$) alkyl group. The ($C_6$–$C_{30}$) alkyl group can be saturated or unsaturated. Polar surfactants that comprise a hydrophobic portion comprising a ($C_6$–$C_{30}$) alkyl group can be determined by one of ordinary skill in the art. Examples of polar surfactants that comprise a hydrophobic portion comprising a ($C_6$–$C_{30}$) alkyl group include, but are not limited to, ($C_6$–$C_{30}$) fatty acid mono and diesters of ethoxylated sorbitan such as PEG-40 diisostearate (e.g. EMSORB™ 2726 PEG-40 Sorbitan Diisostearate (Henkel Corporation (Gulph Mills, Pa.)), PEG-2 sorbitan isostearate, and PEG-40 sorbitan laurate; ($C_6$–$C_{30}$) fatty acid diesters of polyethylene glycol such as PEG-175 distearate and PEG-150 distearate (e.g., LIPOPEG™ 6000-DS (Lipo Chemicals Inc. (Paterson, N.J.)); sodium salts of ($C_6$–$C_{30}$) fatty acyl sarcosinates such as sodium lauroyl sarcosinate (e.g., HAMPOSYL™ L-30 (Hampshire (Lexington, Mass.)) and sodium cocoyl sarcosinate (e.g., HAMPOSYL™ C-30 (Hampshire); ($C_6$–$C_{30}$) fatty acyl esters of sarcosine acid such as lauroyl sarcosine (e.g., HAMPOSYL™ L (Hampshire) and oleoyl sarcosine (e.g., HAMPOSYL™ O (Hampshire)); sodium salts of ($C_6$–$C_{30}$) fatty acyl taurates and methyltaurates such as sodium lauroyl taurate, sodium methyl cocoyl taurate (e.g., a surfactant from the TAURANOL™ WS series (Finetex Inc., Elmwood Park, N.J.)), and sodium methyl oleoyl taurate (e.g., a surfactant from the TAURANOL™ M series (Finetex Inc.)); ($C_6$–$C_{30}$) fatty acyl esters of taurine and methyltaurine acid; ($C_6$–$C_{30}$) fatty acyl betaines such as cocamidopropyl betaine (e.g., TEGO™ Betaine ZF and TEGO™ Betaine E (both of Goldschmidt Chemical Corp., Hopewell, Va.)); and ($C_6$–$C_{30}$) fatty acyl quaternary ammonium chlorides such as dimethicone copolyol myristyl ammonium chloride (e.g. PECOSIL™ SM-40, supra). "PEG" in the foregoing examples and throughout this application is an abbreviation for "polyethylene glycol". Other polar surfactants which comprise a ($C_6$–$C_{30}$) alkyl group can be determined by those of ordinary skill in the art.

In general, polar surfactants that comprise a hydrophobic portion selected from the group consisting of a ($C_6$–$C_{30}$) alkyl group and a polymeric silicone group can be found in texts recognized in the art such as *The CTFA International Cosmetic Ingredient Dictionary* (Cosmetics Tioleteries and Fragrances Association (Washington D.C.)), which is hereby incorporated by reference in its entirety.

The following procedure can, moreover, be used to screen surfactants, such as those ascertained from *The CTFA International Cosmetic Ingredient Dictionary*, above, for use in inhibiting formation of a potassium lauryl sulfate salt according to the present invention. The procedure is based on a three part system of surfactant, TKPP (tetrapotassium pyrophosphate), and SLS in water. The surfactant to be tested is weighed out into 250 ml beakers in increasing increments of 0.5 g: i.e., 0.5 g, 1.0 g, 2.0 g, 2.5 g, etc. 90 ml of a TKPP solution is then added and the solution stirred to dissolve the surfactant. (If the surfactant being tested is itself not soluble in the TKPP solution upon visual inspection, i.e. if the solution appears turbid or a precipitate is observed, then other solvents, such as alcohol, can be included in each beaker to dissolve the surfactant). 10 ml of 4.0% SLS solution is then added with stirring. Since this is a ten fold dilution, the final concentration of SLS in the beaker is 0.4%. The concentration of surfactant in each beaker is deemed equal to the number of grams of surfactant in each beaker, without taking into account the concentration of the surfactant as originally added to the beaker. (Each surfactant is often tested as a 30% concentrate). The series of solutions is allowed to stand for at least four hours. The solution with the lowest concentration of surfactant that is clear is then designated the typical effective concentration. The typical effective concentration of the pure surfactant can then be calculated by multiplying the experimentally-determined typical effective concentration by the actual percentage of surfactant in the originally-added surfactant concentrate.

In a specific embodiment, a composition of the present invention is an oral composition for reducing dental nerve and/or dentin sensitivity in the form of a dentifrice, for example a paste or a gel. Such a composition can comprise potassium nitrate in an amount effective to reduce dental nerve and/or dentin sensitivity when the composition is orally applied to a dental surface, preferably also including a soluble fluoride salt or a soluble monofluorophosphate salt in an amount effective to prevent cavities.

In another embodiment, a composition of the present invention is an oral composition for removing or loosening plaque and/or stains from dental surfaces in the form of an oral rinse, such as a prebrushing rinse, or in the form of a dentifrice.

A preferred dentifrice of the present invention is in the form of a gel, a "liquid gel" being especially preferred. A liquid gel refers to a gel, as defined above, of low viscosity rendering it suitable for rinsing.

An oral rinse of the present invention is preferably in the form of a liquid gel or of a liquid.

A specific dentifrice of the present invention for reducing dental nerve and/or dentin sensitivity comprises:
(a) from about 1% to about 10% potassium nitrate;
(b) from about 0.1% to about 5% SLS;
(c) from about 0.1% to about 20% by weight of an orally-acceptable polar surfactant, said surfactant comprising a hydrophobic portion selected from the group consisting of a ($C_6$–$C_{30}$) alkyl group and a polymeric silicone group;
(d) from about 10% to about 60% by weight of an abrasive silica;
(e) an effective amount of a soluble fluoride salt; and
(f) an orally-acceptable aqueous vehicle;
wherein the molar ratio of the surfactant of (c) to SLS of (b) is greater than or equal to about 1:1.

Another specific dentifrice of the present invention is in the form of a gel and is especially useful for removing or loosening plaque and/or stains from dental surfaces. This dentifrice comprises:
(a) from about 1% to about 10% of a soluble potassium salt selected from the group consisting of dipotassium pyrophosphate, tetrapotassium pyrophosphate, tripotassium pyrophosphate, monopotassium pyrophosphate, and combinations thereof;
(b) from about 0.1% to about 5% SLS;
(c) from about 0.1% to about 20% by weight of an orally-acceptable polar surfactant, said surfactant comprising a hydrophobic portion selected from the group consisting of a ($C_6$–$C_{30}$) alkyl group and a polymeric silicone group;
(d) from about 10% to about 60% by weight of an abrasive silica;
(e) an effective amount of a soluble fluoride salt; and
(f) an orally-acceptable aqueous vehicle;
wherein the molar ratio of the surfactant of (c) to SLS of (b) is greater than or equal to about 1:1.

A specific oral rinse of the present invention for reducing dental nerve and/or dentin sensitivity comprises:
(a) from about 0.1% to about 5% potassium nitrate;
(b) from about 0.02% to about 2% SLS;
(c) from about 0.1% to about 20% by weight of an orally-acceptable polar surfactant, said surfactant comprising a hydrophobic portion selected from the group consisting of a ($C_6$–$C_{30}$) alkyl group and a polymeric silicone group; and
(d) an orally-acceptable aqueous vehicle;
wherein the molar ratio of the surfactant of (c) to SLS of (b) is greater than or equal to about 1:1.

Another specific oral rinse of the present invention especially useful for removing or loosening plaque and/or stains from dental surfaces comprises:
a) from about 0.1% to about 5% of a potassium salt selected from the group consisting of dipotassium pyrophosphate, tetrapotassium pyrophosphate, tripotassium pyrophosphate, monopotassium pyrophosphate, and combinations thereof;
(b) from about 0.02% to about 2% SLS;
(c) from about 0.1% to about 20% by weight of an orally-acceptable polar surfactant, said surfactant comprising a hydrophobic portion selected from the group consisting of a ($C_6$–C30) alkyl group and a polymeric silicone group; and
(d) an orally-acceptable aqueous vehicle;
wherein the molar ratio of the surfactant of (c) to SLS of (b) is greater than or equal to about 1:1.

Flavorings can also optionally be included in the compositions of the subject invention. The flavoring can comprise synthetic chemicals, purified chemicals, natural extracts, or combinations thereof. Examples of flavorings which can be used include, but are not limited to, peppermint; spearmint; wintergreen; clove; cinnamon; anise; sassafras; bubble gum; or fruit flavoring such as lemon, orange, lime, or cherry; or combinations thereof. An "amount of a flavoring effective to provide flavor to a composition", for purposes of this invention, means any amount at which the flavor of the flavoring can be tasted by a subject using the oral composition comprising the flavoring. One of ordinary skill can determine an amount of a flavoring effective to provide flavor to a composition by using known techniques. Various factors known in the art, such as for example the type of flavoring, can be considered when determining the effective amount of any flavoring. Generally, the amount of flavoring that is effective ranges from about 0.001% to about 0.5% of a liquid composition according to the subject invention, and from about 0.25% to about 5% of a paste or gel of the subject invention. Preferred amounts of a flavoring for a liquid range from about .01% to about 0.3% and for a paste or gel from about 0.5% to about 2.5%.

Also provided by the present invention are oral compositions for reducing dental nerve and/or dentin sensitivity which comprise particular flavorings, namely ones that do not comprise a substantial amount of menthol. Such compositions are useful because they do not aggravate sensitive dental nerves and/or dentin as much as oral compositions for sensitive teeth and/or gums which comprise menthol-containing ingredients. In this aspect of the invention, the ingredient which possesses activity in reducing dental nerve and/or dentin sensitivity may be a potassium salt, for example potassium chloride, potassium nitrate, potassium bicarbonate, or another potassium salt noted above as having activity in reducing dental nerve and/or dentin sensitivity, or it may be one or more other substances capable of reducing dental nerve and/or dentin sensitivity, such as strontium chloride or another soluble salt of strontium, or a soluble stannus salt. Other substances which possess activity in reducing dental nerve and/or dentin sensitivity are known in the art and may be used in this aspect of the invention. The composition can comprise a combination of ingredients that each reduces dental nerve and/or dentin sensitivity. An "effective amount" of the ingredient which possesses activity in reducing dental nerve and/or dentin sensitivity, for example potassium chloride, potassium nitrate, and potassium bicarbonate, is any amount which is able to reduce dental nerve and/or dentin sensitivity when the composition is orally applied to a dental surface. Effective amounts of ingredients that reduce dental nerve and/or dentin sensitivity are known in the art and generally are in the range of from about 0.1% to about 20% by weight of the composition. A preferred amount of an ingredient that reduces dental nerve and/or dentin sensitivity is from about 0.05% to about 10%.

A flavoring that "does not contain a substantial amount of menthol", for purposes of the subject invention and unless otherwise indicated, is any flavoring that does not contain a sufficient amount of menthol to aggravate a sensitive dental nerve or sensitive dentin when used in an oral composition in an amount effective to provide flavor to the composition. A flavoring which does not contain a sufficient amount of menthol to aggravate a sensitive dental nerve or sensitive dentin can be determined by one of ordinary skill, for example by orally applying to a dental surface of a sensitive tooth a composition comprising an amount of a flavoring effective to provide flavor to the composition, and determining if the composition aggravates the sensitive nerve or dentin of the tooth, thereby determining if the flavoring contains a sufficient amount of menthol to aggravate a sensitive dental nerve or sensitive dentin. Some flavorings are generally known in the art to contain no menthol, and such flavorings would therefore not have to be tested to determine if they can be used in the subject invention. Other flavorings can be prepared so as to not contain a substantial amount of menthol. Accordingly, the subject invention also provides a mint flavoring that does not comprise a substantial amount. of menthol, said mint flavoring being either a dementholated natural mint extract or a synthetic blend. In one embodiment, a composition of the subject invention for reducing dental nerve and/or dentin sensitivity comprises a flavoring which contains from about 0 to about less than 0.05% menthol. Preferably the amount of menthol is less than about 0.01%.

Methods for obtaining flavorings are known in the art and any such method can be used to obtain a flavoring for the subject invention, provided the flavoring does not contain a substantial amount of menthol. For example, certain mints, i.e., peppermint are known to naturally comprise menthol, and therefore a peppermint flavoring must be either dementholated or synthesized by. blending chemical components (excluding a substantial amount of menthol) in order to be useful for practicing this aspect of the subject invention.

In one embodiment, the flavoring in the sensitivity compositions of this invention does not contain a mint flavoring. Examples of flavoring that are not mint flavorings include, but are not limited to, clove; cinnamon; anise; sassafras; bubble gum; and fruit flavorings, such as, but not limited to, lemon, orange, lime, and cherry.

In another embodiment, however, the flavoring in the sensitivity compositions of the subject invention is a mint flavoring that does not comprise a substantial amount of menthol. Such flavorings are preferred in the sensitivity compositions of the subject invention since many consumers prefer mint flavorings to other types of flavorings. Some mints, such as spearmint, naturally do not contain menthol. Peppermint however, as discussed above, comprises menthol. Any peppermint flavoring, including peppermint used in a mixture of flavorings (for example, a blend of spearmint plus peppermint), must either be dementholated or prepared by blending chemical components before use in this aspect of the subject invention.

The term "dementholated" means all or part of the menthol from a natural mint extract has been chemically removed. Methods of dementholation are known in the art and generally involve cooling the raw oil that is obtained from the *mentha arvensis* plant from a temperature of around 40° C. to just over 0° C. for a period of from about ten to about fourteen days and separating the crystals formed during this period, which consist essentially of menthol, from the residual oil (see, e.g., Haarmann & Reimer (Springfield, N.J.), *Optamint—Freshness with taste to match*). Any natural mint (which naturally contains menthol, such as peppermint) used in accordance with the present invention so as not to unduly aggravate sensitive teeth must be sufficiently dementholated so as to not contain a substantial amount of menthol.

Preferably, however, mint, including peppermint, used in a composition of the subject invention for reducing dental nerve and/or dentin sensitivity is synthesized by blending chemical components, excluding a substantial amount of menthol, i.e. it is a "synthetic blend".

For purposes of this invention, the term "synthetic blend" refers to a flavoring prepared by blending chemical components. The synthetic blend can comprise synthetic chemical components, purified chemical components, or combinations thereof. A "synthetic chemical" for purposes of this invention, unless otherwise indicated, means a chemical that is synthesized from non-natural sources. Synthetic chemicals can, however, be chemically the same as chemicals which are found in natural sources. A synthetic chemical can on the other hand be a molecule which is not found in nature. A "purified chemical" for purposes of this invention, unless otherwise indicated, is a chemical which has been substantially purified from a natural source such as a plant. Known methods of organic synthesis and purification can be used to obtain the synthetic and purified chemicals for the synthetic blends of the present invention. Blending of synthetic and purified chemicals to obtain flavorings which are synthetic blends is also known in the art.

A synthetic blend for use in the subject invention can possess a natural-like taste, for example a synthetic blend that has a peppermint taste; or it can possess a taste that does not occur in nature, for example a synthetic blend that has a wintergreen taste or an orange-mint taste. In general, synthetic blends, including mint flavoring which are synthetic blends, are more preferable than natural extracts for use as flavorings in the sensitivity compositions of the present invention.

As used herein, unless otherwise indicated, the terms "mint", "mint flavoring", and the like, refer to flavorings that have a mint taste, either a natural or natural-like mint taste such as a peppermint taste or spearmint taste, or a mint taste that does not naturally occur such as a wintergreen taste.

The orally-acceptable aqueous vehicle for the detergent compositions of the present invention can be, for example, water or a mixture of water and an orally-acceptable alcohol such as ethanol. An oral rinse of the present invention more specifically comprises from about 50% by weight to about 85% by weight of water based on the total weight of the composition, and, optionally, from about 5% to about 25% ethanol. Not all compositions of this invention, including oral rinses, comprise an alcohol however, and, in same cases, such as in compositions for reducing dental nerve and/or dentin sensitivity, absence of alcohol is preferred.

In certain compositions of the invention, especially those containing no alcohol or a low alcohol content, it may be desirable to include preservatives, for example benzoic acid, sodium benzoate, methylparaben, propylparaben, sorbic acid, potassium sorbate, or combinations thereof. Other preservatives known in the art to be useful in detergent compositions can be used in the compositions of the present invention. The amount of preservative is generally within the range of from about 0% to about 2%, and preferably from about 0.01% to about 1%.

Examples of abrasives useful in dentifrices of the subject invention include, but are not limited to, abrasive silica such as precipitated silica or silica gels preferably having an average particle size ranging from about 0.1 to about 50 microns. Preferred silica abrasives include those marketed under the tradename SYLODENT™ or SYLOID™ by the W. R. Grace & Co. and those marketed under the tradename ZEODENT™ by the J. M. Huber Corp. Other suitable abrasives include, but are not limited to, β-phase calcium pyrophosphate, alumina and calcium carbonate. Other abrasives can be used in the present invention. The amount of abrasive in a dentifrice composition ranges up to about 60% by weight, preferably from 10% by weight to 40% by weight.

Oral compositions of the present invention can optionally comprise humectants, which can impart a moist feeling to the mouth and, in some cases, can sweeten the compositions. Humectants useful in the oral compositions of the present invention include, but are not limited to, edible polyhydric alcohols such as glycerin, sorbitol, propylene glycol, xylitol, and cyclodextrins, including their derivatives. Other humectants known in the art can be used in the compositions of this invention. A humectant generally is present in an amount of from about 0.1% to about 30% for oral rinses and from about 10% to about 50% for dentifrices. If a humectant is included in an oral rinse of this invention, it is preferably present in an amount of from about 5% to about 25%.

The oral compositions of the present invention can further comprise an effective amount of a soluble fluoride salt, for example sodium fluoride, potassium fluoride, or stannous fluoride; or a soluble monofluorophosphate salt such as sodium monofluorophosphate. An effective amount of a soluble fluoride salt or soluble sodium monofluorophosphate salt for a composition of the present invention is an amount that is effective in preventing cavities, generally an amount sufficient to provide from about 50 ppm to about 2,500 ppm fluoride ion to the composition; determining such an effective amount is within the ordinary skill in the art. "Preventing cavities" means treating the teeth so that they are less prone to cavity formation.

Compositions of this invention can also optionally comprise thickening agents and/or binders. Typical thickening agents include, but are not limited to, xanthan gum, carrageenan, carboxyvinyl polymers, carbomers, cellulose gums such as carboxymethyl cellulose, cellulose derivatives such as hydroxyethylcellulose and silicas. Thickeners are usually present in the compositions in an amount of up to about 20%. Xanthan gum is a preferred thickener for an oral rinse. In dentifrices, silica-based thickeners, such as SYLOX™ (W. R. Grace & Co., Boca Raton, Fla.), can be used.

Examples of sweeteners that can optionally be included in the compositions of the present invention include, but are not limited to, saccharin, lactose, maltose, aspartame, acesulfame potassium (Nutrinova (Somerset, N.J., USA), sodium cyclamate, and polydextrose.

Coloring agents, including those acceptable for oral use, known in the art can also be used in the compositions of the present invention. Generally, a coloring agent is present in a composition of this invention in an amount of up to about 0.01%.

The compositions of the present invention can optionally contain other ingredients, for example fragrances, known in the art to be useful in detergent compositions for use in healthcare or as surface or fabric cleaners.

The stability of the detergent compositions of the present invention at low temperatures can be determined by cooling a composition to about 35° F., storing the composition at such temperature for about seven days, and then evaluating the composition for the presence or absence of any precipitate, such as crystals or flocculated material, after warming the cooled composition to a temperature of about room temperature. The stability of the compositions of the invention over time at room temperature can also be evaluated according to the above criterion, i.e., absence of precipitate, such as crystals or flocculated material.

The following examples are provided to merely illustrate aspects of the subject invention. They are not intended to, and should not be construed to, limit the invention set forth in the claims and more fully described herein.

EXAMPLE 1

Eight surfactants were formulated into oral rinses (Formulations A–H) according to the present invention, as indicated in the following Table 1. The amounts of ingredients in Table 1 are weight percent, based on the total weight of the formulation. "TKPP" is tetrapotassium pyrophosphate, and "TSPP" is tetrasodium pyrophosphate; thus, each formulation contains 1% by weight of the pyrophosphate anion $P_2O_7^{4-}$, 75% of which is TKPP.

TABLE 1

| Ingredient | A | B | C | D | E | F | G | H |
|---|---|---|---|---|---|---|---|---|
| Part A: | | | | | | | | |
| Water | 60.00 | 60.00 | 60.00 | 60.00 | 60.00 | 60.00 | 60.00 | 60.00 |
| Xanthan Gum | 0.03 | 0.03 | 0.03 | 0.03 | 0.03 | 0.03 | 0.03 | 0.03 |
| TKPP | 1.42 | 1.42 | 1.42 | 1.42 | 1.42 | 1.42 | 1.42 | 1.42 |
| TSPP | 0.38 | 0.38 | 0.38 | 0.38 | 0.38 | 0.38 | 0.38 | 0.38 |
| Benzoic Acid | 0.53 | 0.53 | 0.53 | 0.53 | 0.53 | 0.53 | 0.53 | 0.53 |
| Poloxomar 407 | 0.30 | 0.30 | 0.30 | 0.30 | 0.30 | 0.30 | 0.30 | 0.30 |
| Na Benzoate | 0.37 | 0.37 | 0.37 | 0.37 | 0.37 | 0.37 | 0.37 | 0.37 |
| Na Saccharin | 0.03 | 0.03 | 0.03 | 0.03 | 0.03 | 0.03 | 0.03 | 0.03 |
| Sorbitol (70%) | 20.00 | 20.00 | 20.00 | 20.00 | 20.00 | 20.00 | 20.00 | 20.00 |
| Part B: | | | | | | | | |
| Water | 7.0 | 7.0 | 7.0 | 7.0 | 7.0 | 7.0 | 7.0 | 7.0 |
| Alcohol (190 pf) | 7.0 | 7.0 | 7.0 | 7.0 | 7.0 | 7.0 | 7.0 | 7.0 |
| SLS | 0.4 | 0.4 | 0.4 | 0.4 | 0.4 | 0.4 | 0.4 | 0.4 |
| surfactant* | 1.5 | 1.5 | 1.5 | 1.0 | 1.0 | 1.0 | 0.75 | 0.5 |
| flavoring | 0.18 | 0.18 | 0.18 | 0.15 | 0.15 | 0.15 | 0.18 | 0.18 |
| water | qs | qs | Qs | qs | qs | qs | qs | qs |
| Total | 100 | 100 | 100 | 100 | 100 | 100 | 100 | 100 |

*The surfactant used in each formulation was:
Formulation A, HAMPOSYL L-30 (Sodium Lauroyl Sarcosinate);
Formulation B, EMSORB 2726 (PEG 40 Sorbitan Diisostearate);
Formulation C, Betaine ZF (CocamidopropylBetaine/Cocamidopropyl);
Formulation D, PECOSIL DCT (SodiumDimethiconeCopolyolAcetyl/MethylTaurate);
Formulation E, PECOSIL SM-40 (Dimethicone Copolyol Myristyl Ammonium Chloride);
Formulation F, PECOSIL PS-100 (Dimethicone Copolyolphosphate);
Formulation G, TAURANOL WS (Ethanesulfonic acid, 20(methylamino)-N-Cocoacyl); and
Formulation H, LIPOPEG 6000D5 (PEG-150 Distearate).

Formulations A–H were prepared in general according to the following procedure:

Part A was first prepared: Xanthan gum was dispersed in 60 wt % water and mixed for 15 minutes under high shear. The tetrapotassium pyrophosphate, tetrasodium pyrophosphate, and benzoic acid were added to the Xanthan gum dispersion and the resulting mixture mixed for 15 minutes or until dissolved. The Poloxamer 407, sodium benzoate, sodium saccharin, and sorbitol were added, and the resulting mixture was then mixed; the resulting Part A was then mixed for 20 minutes.

Part B was prepared next: The sodium lauryl sulfate was dissolved in alcohol and 7 wt % water; this mixture was then mixed for 15 minutes or until the SLS dissolved. The surfactant was added and the resulting mixture mixed for 10 minutes. The flavor was added and the resulting mixture then mixed for 10 minutes. The remaining water was added, and the resulting Part B mixed for 10 minutes.

Part B was slowly added to Part A and the resulting mixture mixed for 20 minutes.

The pH of each finished formulation was in the range of about 7.0 to about 8.0.

The above Formulations A–H were still clear after approximately one year or more at room temperature.

EXAMPLE 2

The following Formulation I is one example of an oral rinse for reducing dental nerve and/or dentin sensitivity according to the subject invention. The pH of Formulation I is within the range of from about 5.0 to about 7.0:

Formulation I

| Ingredient | wt./wt. % |
|---|---|
| Water | 60.010 |
| Xanthan Gum | 0.035 |
| Potassium Nitrate | 1.000 |
| HAMPOSYL ™ L-30 (30.0%) | 2.000 |
| Sodium Saccharin | 0.030 |
| Sorbitol (70%) | 20.000 |
| Aloe powder | 0.250 |
| Sodium salicylate | 2.000 |
| Disodium Phosphate | 0.025 |
| Monosodium Phosphate | 0.100 |
| Alcohol (190 pf) | 7.000 |
| Water | 7.000 |
| SLS | 0.400 |
| Flavoring | 0.150 |
| | 100.000% |

Formulation I was prepared by as follows: The xanthan gum was dispersed in 60.010 wt % water and mixed for 15 minutes under high shear. The $KNO_3$ was added and mixed until dissolved. Hamposyl L-30, sodium saccharin, sorbitol, aloe powder, and sodium salicylate were added; the resulting mixture was mixed for 20 minutes. The disodium phosphate and monosodium phosphate were added; the resulting mixture was then mixed for 10 minutes. In a separate container, the alcohol, 7.0 wt % water, SLS, and flavor were combined until the SLS dissolved. The alcohol/water/SLS/flavor mixture was added to the batch and mixed for 15 minutes.

EXAMPLE 3

The following Formulation J is one example of a dentifrice according to the subject invention, in the form of a liquid gel, for reducing dental nerve and/or dentin sensitivity:

Formulation J

| Ingredient | wt./wt. % |
|---|---|
| Hydroxy EthylCellulose | 1.000% |
| PEG-8 | 3.000 |
| Glycerin (99.5%) | 10.000 |
| Purified Water | 18.000 |
| Potassium Nitrate | 5.000 |
| Sodium Fluoride | 0.243 |
| HAMPOSYL ™ L-30 (30%) | 4.000 |
| Xanthan Gum | 0.300 |
| Sorbitol (70%) | 35.451 |
| Sodium Saccharin | 0.500 |
| SYLODENT ™ 15 (thickening silica from W.R. Grace & Co.) | 8.000 |
| SYLODENT ™ 750 (abrasive silica from W. R. Grace & Co.) | 10.000 |

-continued

| Formulation J | |
|---|---|
| Ingredient | wt./wt. % |
| Dye(s) | 0.006 |
| SLS (30% solution) | 3.000 |
| Flavoring | 1.500 |
| | 100.000% |

Formulation J was prepared as follows: The carboxyethyl cellulose was dispersed in the PEG-8 and glycerin using a mixer. In a separate container, the $KNO_3$ was dissolved in the water and sorbitol and mixed until dissolved. NaF was added to the water mixture and mixing was continued for 25 minutes. The water/sorbitol/$KNO_3$/NaF phase was added to the caroboxyethyl cellulose/PEG-8/glycerin mixture and mixed for 10 minutes. The xanthan gum was slowly added and mixed under high shear for 15 minutes. Hamposyl L-30, sodium saccharin, Sylodent 15, Sylodent 750, dyes (FD&C Blue #1 and D&C Yellow #10) were added; this resulting mixture was mixed until homogenous. The flavor was dissolved in the SLS and mixed for 5 minutes. The flavor/SLS mixture was added to the batch and mixed for 10 minutes. The resulting gel was deaerated to remove entrapped air bubbles.

What is claimed is:

1. An oral mouthrinse composition for reducing nerve sensitivity comprising:
   (a) from about 0.01% by weight to about 5% by weight of an orally-acceptable, soluble potassium salt;
   (b) from about 0.01% by weight to about 10% by weight of a sodium ($C_8$–$C_{24}$) alkylsulfate;
   (c) from about 0.01% by weight to about 20% by weight of an orally-acceptable polar surfactant, said surfactant selected from the group consisting of a $C_6$–$C_{30}$), fatty acid mono or diester of ethoxylated sorbitan, a ($C_6$–$C_{30}$) fatty acid diester of polyethylene glycol, a sodium salt of a ($C_6$–$C_{30}$) fatty acyl sarcosinate, a ($C_6$–$C_{30}$) fatty acyl ester of sarcosine acid, a sodium salt of a ($C_6$–$C_{30}$) fatty acyl taurate, a sodium salt of a ($C_6$–$C_{30}$) fatty acyl methyltaurate, a ($C_6$–$C_{30}$) fatty acyl ester of taurine, a ($C_6$–$C_{30}$) fatty acyl ester of methyltaurine acid, a ($C_6$–$C_{30}$) fatty acyl betaine, a ($C_6$–$C_{30}$) fatty acyl quaternary ammonium chloride, dimethicone copolyols, polydimethylsiloxane phosphate esters, polydimethylsiloxane copolyol phosphate esters, polydimethylsiloxane phosphobetaines, polydimethylsiloxane copolyol phosphobetaines, polydimethylsiloxane taurates, polydimethylsiloxane copolyol taurates, acetylated polydimethylsiloxane copolyols, and polydimethylsiloxane quaternium compounds, polydimethylsiloxane copolyol quaternium compounds; and
   (d) an orally-acceptable aqueous vehicle comprising from about 50% to about 85% water; wherein the potassium salt is dissolved in the composition and wherein the molar ratio of the surfactant of (c) to the sodium ($C_8$–$C_{24}$) alkylsulfate is greater than or equal to about 1:1 such that when a.), b.), a.) are dissolved in d.), the resultant composition is clear.

2. The oral mouthrinse composition according to claim 1, wherein the soluble potassium salt of the composition comprises a potassium pyrophosphate salt in an amount effective, optionally in combination with other pyrophosphate salts, to remove or loosen plaque and/or stains when the composition is orally applied to a dental surface.

3. The oral mouthrinse composition according to claim 1, wherein the soluble potassium salt of the composition comprises soluble potassium salt that possesses activity in reducing dental nerve and/or dentin sensitivity in an amount effective to reduce dental nerve and/or dentin sensitivity when the composition is orally applied to a dental surface.

4. The oral mouthrinse composition according to claim 3, wherein the soluble potassium salt that possesses activity in reducing dental nerve and/or dentin sensitivity is potassium nitrate.

5. The oral mouthrinse composition according to claim 3, further comprising a flavoring that does not comprise a substantial amount of menthol.

6. The oral mouthrinse composition according to claim 5 wherein the flavoring that does not comprise a substantial amount of menthol is a mint flavoring.

7. The oral monthrinse composition according to claim 1, wherein the soluble potassium salt is selected from the group consisting of a potassium pyrophosphate salt, potassium nitrate, and mixtures thereof.

8. An oral composition in the form of a rinse for reducing dental nerve and/or dentin sensitivity comprising
   (a) from about 0.1% to about 5% potassium nitrate;
   (b) from about 0.02% to about 2% SLS;
   (c) from about 0.1% to about 20% by weight of an orally-acceptable polar surfactant, said surfactant selected from the group consisting of a ($C_6$–$C_{30}$) fatty acid mono diester of ethoxylated sorbitan, a ($C_6$–$C_{30}$) fatty acid diester of polyethylene glycol, a sodium salt of a ($C_{6-C30}$) fatty acyl sarcosinate, a ($C_6$–$C_{30}$) fatty acyl ester of sarcosine acid, a sodium salt of a ($C_6$–$C_{30}$) fatty acyl taurate, a sodium salt of a ($C_6$–$C_{30}$) fatty acyl methyltaurate, a ($C_6$–$C_{30}$) fatty acyl ester of taurine, a ($C_6$–$C_{30}$) fatty acyl ester of methyltaurine acid, a ($C_6$–$C_{30}$) fatty acyl betaine, a ($C_6$–$C_{30}$) fatty quaternary ammonium chloride, dimethicone copolyols, polydimethylsiloxane phosphate esters, polydimethylsiloxane copolyol phosphate esters, polydimethylsiloxane phosphobetaines, polydimethylsiloxane, copolyol phosphobetaines, polydimethylsiloxane taurates, polydimethylsiloxane copolyol taurates, acetylated polydimethylsiloxane copolyols, and polydimethylsiloxane quaternium compounds, polydimethylsiloxane copolyol quaternium compounds; and
   (d) an orally-acceptable aqueous vehicle comprising from about 50% to about 85% water; wherein the potassium salt is dissolved in the composition and wherein the molar ratio of the surfactant of (c) to the sodium ($C_8$–$C_{24}$) alkylsulfate is greater than or equal to about 1:1 such that when a.), b.), c.) are dissolved in d.), the resultant composition is clear.

9. An oral composition in the form of a rinse for removing or loosening plaque and/or stains from dental surfaces comprising
   (a) from about 0.1% to about 5% of a potassium salt selected from the group consisting of dipotassium pyrophosphate, tetrapotassium pyrophosphate, tripotassium pyrophosphate, monopotassium pyrophosphate, and combinations thereof;
   (b) from about 0.02% to about 2% SLS;
   (c) from about 0.1% to about 20% by weight of an orally-acceptable polar surfactant, said surfactant selected from the group consisting of a ($C_6$–$C_{30}$) fatty acid mono or diester of ethoxylate sorbitan, a ($C_6$–$C_{30}$) fatty acid diester of polyethylene glycol, a sodium salt of a ($C_6$–$C_{30}$) fatty acyl sarcosinate, a ($C_6$–$C_{30}$) fatty acyl ester of sarcosine acid, a sodium salt of a ($C_6$–$C_{30}$) fatty acyl taurate, a sodium salt of a ($C_6$–$C_{30}$) fatty acyl methyltaurate, a ($C_6$–$C_{30}$) fatty acyl ester of taurine, a ($C_6$–$C_{30}$) fatty acyl ester of methyltaurine acid, a ($C_6$–$C_{30}$) fatty acyl betaine, a ($C_6$–$C_{30}$) fatty acyl quaternary ammonium chloride, dimethicone copolyols, polydimethylsiloxane phosphate esters, polydimethylsiloxane copolyol phospohate esters, polydimethylsiloxane phosphobetaines, polydimethylsiloxane copolyol phosphobetaines, polydimethylsiloxane taurates, polydimethylsiloxane copolyol taurates, acetylated polydimethylsiloxane copolyols, and polydimethylsiloxane quaternium compounds, polydimethylsiloxane copolyol quaternium compounds; and (d) an orally-acceptable aqueous vehicle comprising from about 50% to about 85% water; wherein the potassium salt is dissolved in the composition and wherein the molar ratio of the surfactant of (c) to the sodium ($C_8$–$C_{24}$) alkylsulfate is greater than or equal to about 1:1 such that when a.), b.), c.) are dissolved in d.), the resultant composition is clear.

* * * * *

UNITED STATES PATENT AND TRADEMARK OFFICE
CERTIFICATE OF CORRECTION

PATENT NO. : 7,153,493 B2
APPLICATION NO. : 10/630526
DATED : December 26, 2006
INVENTOR(S) : Nelson et al.

It is certified that error appears in the above-identified patent and that said Letters Patent is hereby corrected as shown below:

Col. 17, Line 62, delete "a.), b.), a.)" and substitute -- a.), b.), c.) --.

Signed and Sealed this

Twenty-fourth Day of June, 2008

JON W. DUDAS
*Director of the United States Patent and Trademark Office*